(12) United States Patent
Qi

(10) Patent No.: US 11,055,512 B2
(45) Date of Patent: Jul. 6, 2021

(54) METHOD, APPARATUS AND SERVER FOR DETERMINING MENTAL STATE OF HUMAN

(71) Applicant: BAIDU ONLINE NETWORK TECHNOLOGY (BEIJING) CO., LTD., Beijing (CN)

(72) Inventor: Tianyu Qi, Beijing (CN)

(73) Assignee: BAIDU ONLINE NETWORK TECHNOLOGY (BEIJING) CO., LTD.

(*) Notice: Subject to any disclaimer, the term of this patent is extended or adjusted under 35 U.S.C. 154(b) by 133 days.

(21) Appl. No.: 16/517,928

(22) Filed: Jul. 22, 2019

(65) Prior Publication Data
US 2019/0347471 A1 Nov. 14, 2019

(30) Foreign Application Priority Data

Aug. 6, 2018 (CN) .......................... 201810886488.0

(51) Int. Cl.
G06K 9/00 (2006.01)
G16H 50/30 (2018.01)
G06K 9/62 (2006.01)

(52) U.S. Cl.
CPC ....... *G06K 9/00268* (2013.01); *G06K 9/6228* (2013.01); *G06K 9/6256* (2013.01); *G16H 50/30* (2018.01)

(58) Field of Classification Search
CPC ..... A61B 5/1103; A61B 5/163; A61B 5/1114; A61B 8/10; G06K 9/00281;
(Continued)

(56) References Cited

U.S. PATENT DOCUMENTS 7,071,831 B2 * 7/2006 Johns ...................... G08B 21/06
340/576
7,120,880 B1 * 10/2006 Dryer ...................... G06Q 30/02
715/863

(Continued)

FOREIGN PATENT DOCUMENTS

CN 103020594 A 4/2013
CN 106485191 A 3/2017
(Continued)

OTHER PUBLICATIONS

Office Action dated May 7, 2020 in Corresponding Chinese Application No. 201810886488.0, 8 pages.

*Primary Examiner* — Yosef Kassa
(74) *Attorney, Agent, or Firm* — Dilworth IP, LLC

(57) ABSTRACT

An embodiment of the present disclosure provides a method, an apparatus and a server for determining a mental state of a human, which are used for an augmented reality. The method includes: obtaining a to-be-detected picture; extracting face feature information of a target object from the to-be-detected picture; and inputting the face feature information of the target object into a mental state detecting model to obtain a mental state of the target object. The method, the apparatus and the server for determining a mental state of a human provided by the embodiment of the present disclosure improve the accuracy of the obtained mental state while improving the mental state obtaining efficiency.

15 Claims, 5 Drawing Sheets

(58) Field of Classification Search
CPC ............ G06K 9/00335; G06K 9/00845; G06T 11/003; G06T 2207/10016; G06T 7/0012
See application file for complete search history.

(56) References Cited

U.S. PATENT DOCUMENTS

| | | | | |
|---|---|---|---|---|
| 7,515,054 | B2* | 4/2009 | Torch | A61B 3/112 340/573.1 |
| 8,298,078 | B2* | 10/2012 | Sutton | G07F 17/3206 463/29 |
| 8,462,996 | B2* | 6/2013 | Moon | G06K 9/00315 382/118 |
| 8,626,264 | B1* | 1/2014 | Beran | G16H 50/20 600/407 |
| 8,736,760 | B2* | 5/2014 | Ohki | H04N 19/30 348/459 |
| 8,861,815 | B2* | 10/2014 | Cecchi | G16H 50/20 382/128 |
| 9,330,523 | B2* | 5/2016 | Sutton | A61B 5/165 |
| 9,723,992 | B2* | 8/2017 | Senechal | A61B 5/02405 |
| 2009/0003709 | A1 | 1/2009 | Kaneda et al. | |
| 2015/0003672 | A1 | 1/2015 | Sarkis et al. | |

FOREIGN PATENT DOCUMENTS

| | | |
|---|---|---|
| CN | 107578008 A | 1/2018 |
| CN | 107818785 A | 3/2018 |
| CN | 108171176 A | 6/2018 |

* cited by examiner

METHOD, APPARATUS AND SERVER FOR DETERMINING MENTAL STATE OF HUMAN

CROSS-REFERENCE TO RELATED APPLICATIONS

The present disclosure claims priority to Chinese application number 201810886488.0, filed on Aug. 6, 2018, which is incorporated by reference in its entirety.

TECHNICAL FIELD

The present disclosure relates to the field of computer technologies, and in particular, to a method, an apparatus, and a server for determining a mental state of a human.

BACKGROUND

In the prior art, for obtaining a mental state of an object, physiological characteristic information of the object is measured by a measuring device, and the mental state of the object is determined according to the measured physiological characteristic information. However, by this means, the operation process is complex and the measuring device needs to meet strict requirements, which not only makes the mental state obtaining efficiency low, but also makes the obtained mental state less accurate.

SUMMARY

Embodiments of the disclosure provide a method, an apparatus and a server for determining a mental state of a human, which improves the accuracy of the obtained mental state while improving the mental state obtaining efficiency.

In a first aspect, an embodiment of the present disclosure provides a method for determining a mental state of a human, and the method is used for an augmented reality, and includes:
 obtaining a to-be-detected picture;
 extracting face feature information of a target object from the to-be-detected picture; and
 inputting the face feature information of the target object into a mental state detecting model to obtain a mental state of the target object.

In a possible implementation, the face feature information of the target object includes at least one of the following:
 a degree of eye openness, whether red veins exist in an eye, a color of an eye socket, a size of a pouch under the eye, and a state of skin.

In a possible implementation, the inputting the face feature information of the target object into a mental state detecting model to obtain a mental state of the target object includes:
 constructing a feature vector corresponding to the face feature information of the target object; and
 inputting the feature vector into the mental state detecting model to obtain the mental state of the target object.

In a possible implementation, the mental state detecting model is trained by following means:
 constructing, according to the face feature information in each of a plurality of training samples, a feature vector corresponding to each training sample; and
 determining the mental state detecting model according to the feature vector corresponding to each training sample and the mental state labelled in each training sample.

In a possible implementation, the determining the mental state detecting model according to the feature vector corresponding to each training sample and the mental state labelled in each training sample includes:
 training, by using a deep learning method, the feature vector corresponding to each training sample and the mental state labelled in each training sample to obtain the mental state detecting model.

In a possible implementation, after the inputting the face feature information of the target object into a mental state detecting model to obtain a mental state of the target object, the method further includes:
 determining, according to the mental state of the target object and a mapping relationship between the mental state and a state adjustment strategy, a corresponding state adjustment strategy; and
 sending to a terminal, the mental state of the target object and the state adjustment strategy corresponding to the mental state of the target object.

In a second aspect, an embodiment of the present disclosure further provides an apparatus for determining a mental state of a human, and the apparatus is used for an augmented reality, and includes:
 an obtaining unit, configured to obtain a to-be-detected picture;
 the obtaining unit being further configured to extract face feature information of a target object from the to-be-detected picture; and
 a processing unit, configured to input the face feature information of the target object into a mental state detecting model to obtain the mental state of the target object.

In a possible implementation, the face feature information of the target object includes at least one of the following:
 a degree of eye openness, whether red veins exist in an eye, a color of an eye socket, a size of a pouch under the eye, and a state of skin.

In a possible implementation, the processing unit is specifically configured to: construct a feature vector corresponding to the face feature information of the target object; and input the feature vector into the mental state detecting model to obtain the mental state of the target object.

In a possible implementation, the apparatus further includes a constructing unit, and the mental state detecting model is trained by following:
 the constructing unit is configured to construct, according to the face feature information in each of a plurality of training samples, a feature vector corresponding to each training sample; and
 the processing unit is further configured to determine the mental state detecting model according to the feature vector corresponding to each training sample and the mental state labelled in each training sample.

In a possible implementation, the processing unit is specifically configured to train, by using a deep learning method, the feature vector corresponding to each training sample and the mental state labelled in each training sample to obtain the mental state detecting model.

In a possible implementation, the apparatus further includes a sending unit;
 the processing unit is further configured to determine, according to the mental state of the target object and a mapping relationship between a mental state and a state adjustment strategy, a corresponding state adjustment strategy; and the sending unit is configured to send, to a terminal, the mental state of the target object and the state adjustment strategy corresponding to the mental state of the target object.

In a third aspect, an embodiment of the present disclosure further provides a server including a processor and a memory, where the memory is configured to store a program instruction; and the processor is configured to read the program instruction in the memory, and execute the method for determining a mental state of a human illustrated by any one of the implementations of the first aspect, according to the program instruction in the memory.

In a fourth aspect, an embodiment of the present disclosure further provides a computer readable storage medium, where the computer readable storage medium stores a computer program, and the computer program, when executed by a processor, performs the method for determining a mental state of a human illustrated by any one of the implementations of the first aspect.

With the method, the apparatus and the server for determining a mental state of a human provided by the embodiments of the present disclosure, for obtaining the mental state of an object, a to-be-detected picture is firstly obtained, face feature information of the target object is extracted from the to-be-detected picture, and the extracted face feature information of the target object is input into a mental state detecting model to obtain the mental state of the target object according to the mental detecting model, which, in comparison with determining the mental state of the target object by a measuring device in the prior art, does not need to obtain physiological characteristics of the target object via a measuring device, and then to determine the mental state of the target object according to the physiological characteristic information, thereby not only improving the mental state obtaining efficiency, but also improving the accuracy of the obtained mental state.

BRIEF DESCRIPTION OF DRAWINGS

The accompanying drawings, which are incorporated in and constitute a part of the specification, illustrate embodiments of the present disclosure and, together with the description, serve to explain the principles of the disclosure.

Figure 1:
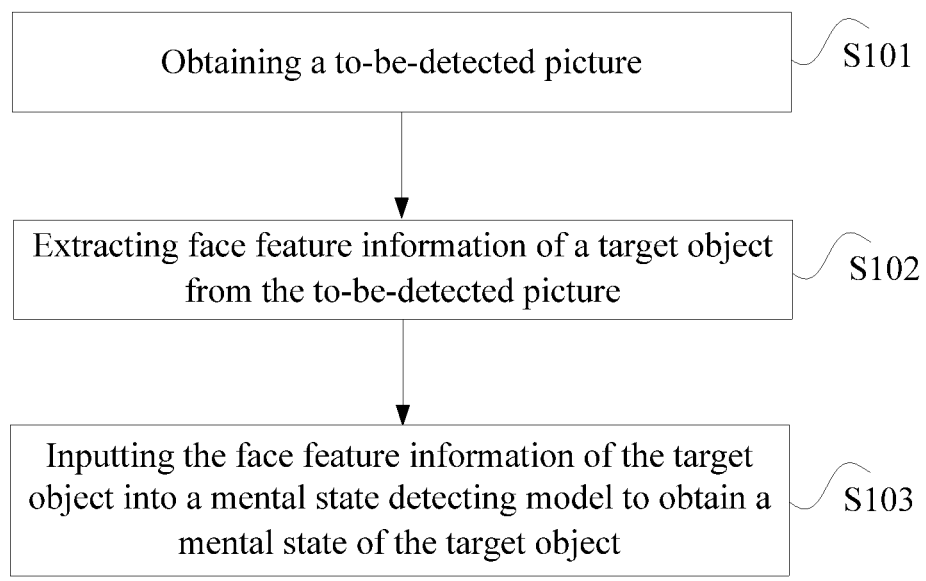
FIG. 1 is a schematic flowchart diagram of a method for determining a mental state of a human according to an embodiment of the present disclosure.

The specific embodiments of the present disclosure have been illustrated by the above drawings, which will be described in more detail below. The drawings and the textual description are not intended to limit the scope of the present disclosure in any way, but to describe the concepts in the present disclosure for those skilled in the art by reference to the specific embodiments.

DESCRIPTION OF EMBODIMENTS

To make the purpose, technical solutions, and advantages of the embodiments of the present disclosure clearer, the technical solutions in the embodiments of the present disclosure are clearly and completely described with reference to the drawings in the embodiments of the present disclosure below. Apparently, the described embodiments are some but not all of the embodiments of the present disclosure. All other embodiments obtained by persons of ordinary skill in the art based on the embodiments of the present disclosure without any creative effort shall fall within the protection scope of the present disclosure.

The terms "first", "second", "third", and "fourth" and the like (if any) in the specification, the claims and the drawings of the present application are used to distinguish different objects, rather than describe a specific order. It is to be understood that data used in this way may be interchanged where appropriate, so that the embodiments of the disclosure described herein can be implemented in a sequence other than those illustrated or described herein. Furthermore, the terms "including", "comprising", "having" and any variation thereof are intended to reference a non-exclusive inclusion. For example, a process, a method, a system, a product, or a device including a series of steps or units is not necessarily limited to the listed steps or units, but optionally also includes other steps or units not listed or inherent to such process, method, product or device.

In the prior art, for obtaining the mental state of an object, physiological characteristic information of the object is measured by a measuring device, and the mental state of the object is determined according to the measured physiological characteristic information, which not only makes the mental state obtaining efficiency low, but also makes the obtained mental state less accurate. In order to improve the accuracy of the obtained mental state, while at the same time improving the mental state obtaining efficiency, the embodiments of the present disclosure provide a method for determining a mental state of a character. For obtaining the mental state of an object, a to-be-detected picture is firstly obtained, face feature information of the target object is extracted from the to-be-detected picture, and the extracted face feature information of the target object is input into a mental state detecting model to obtain the mental state of the target object according to the mental detecting model, which, in comparison with determining the mental state of the target object by a measuring device in the prior art, does not need to obtain physiological characteristics of the target object via a measuring device, and then to determine the mental state of the target object according to the physiological characteristic information, thereby not only improving the mental state obtaining efficiency, but also improving the accuracy of the obtained mental state.

The technical solutions of the present disclosure and how the technical solutions of the present disclosure solve the above technical problems are described in detail below with reference to specific embodiments. The following specific embodiments may be combined with each other, and same or similar concepts or processes are not repeated in some embodiments. The embodiments of the present disclosure will be described below with reference to the accompanying drawings.

FIG. 1 is a schematic flowchart diagram of a method for determining a mental state of a human according to an embodiment of the present disclosure. The method for determining a mental state of a human may be applied to augmented reality, and may be performed by an apparatus for determining a mental state of a human. An operating apparatus of a detect case can be set independently or integrated in a server. For example, the method for determining a mental state of a human may include:

S101: obtaining a to-be-detected picture.

The to-be-detected picture includes face feature information of a target object. In an embodiment, the face feature information of the target object includes at least one of the following: a degree of eye openness, whether red veins exist in an eye, a color of an eye socket, a size of a pouch under the eye, and a state of skin. Further, the state of the skin may include a skin gloss and the like.

For obtaining the to-be-detected picture, the to-be-detected picture may be obtained in advance by a terminal. Of course, the to-be-detected picture may also be obtained in a real-time manner by the terminal. How to obtain the to-be-detected picture is not further limited in the embodiments of the present disclosure.

S102: extracting face feature information of the target object from the to-be-detected picture.

After the to-be-detected picture is obtained through the above S101, the face feature information of the target object can be extracted from the to-be-detected picture, so that the mental state of the target object is determined according to the face feature information of the target object.

In an embodiment, for extracting the face feature information of the target object, it is possible to extract the face feature information of the target object from the to-be-detected picture through a feature extraction technology, and reference may be made to the related description of the feature extraction technology in the prior art, which will not be repeated in the embodiments of the present disclosure.

S103: inputting the face feature information of the target object into a mental state detecting model to obtain the mental state of the target object.

For example, for outputting the mental state of the target object, it is possible to directly output a category of the mental state, such as a very poor mental state, a poor mental state, a general mental state, a good mental state, and a very good mental state. Of course, it is also possible to output a quantized value of the mental state, and the mental state is quantified as a score segment. For example, a score segment of 0-20 points corresponds to the very poor mental state, a score segment of 20-40 points corresponds to the poor mental state, a score segment of 40-60 points corresponds to the general mental state, a score segment of 60-80 points corresponds to the good mental state, and a score segment of 80-100 points corresponds to the very good mental state. Here, these two output modes are only taken as an example for illustration in the embodiments of the present disclosure, but this does not represent that the embodiments of the present disclosure are limited only thereto.

After the face feature information of the target object is extracted through the above S102, the extracted face feature information of the target object can be input into a predetermined mental state detecting model, and a output result of the mental state detecting model is the mental state of the target object, thus the mental state of the target object is obtained, which, in comparison with determining the mental state of the target object by a measuring device in the prior art, does not need to first obtain physiological characteristics of the target object via a measuring device, and then to determine the mental state of the target object according to the physiological characteristic information, thereby not only improving the mental state obtaining efficiency, but also improving the accuracy of the obtained mental state.

With the method for determining a mental state of a human provided by the embodiment of the present disclosure, for obtaining the mental state of an object, a to-be-detected picture is firstly obtained, face feature information of the target object is extracted from the to-be-detected picture, and the extracted face feature information of the target object is input into a mental state detecting model to obtain the mental state of the target object according to the mental detecting model, which, in comparison with determining the mental state of the target object by a measuring device in the prior art, does not need to obtain physiological characteristics of the target object via a measuring device, and then to determine the mental state of the target object according to the physiological characteristic information, thereby not only improving the mental state obtaining efficiency, but also improving the accuracy of the obtained mental state.

Figure 2:
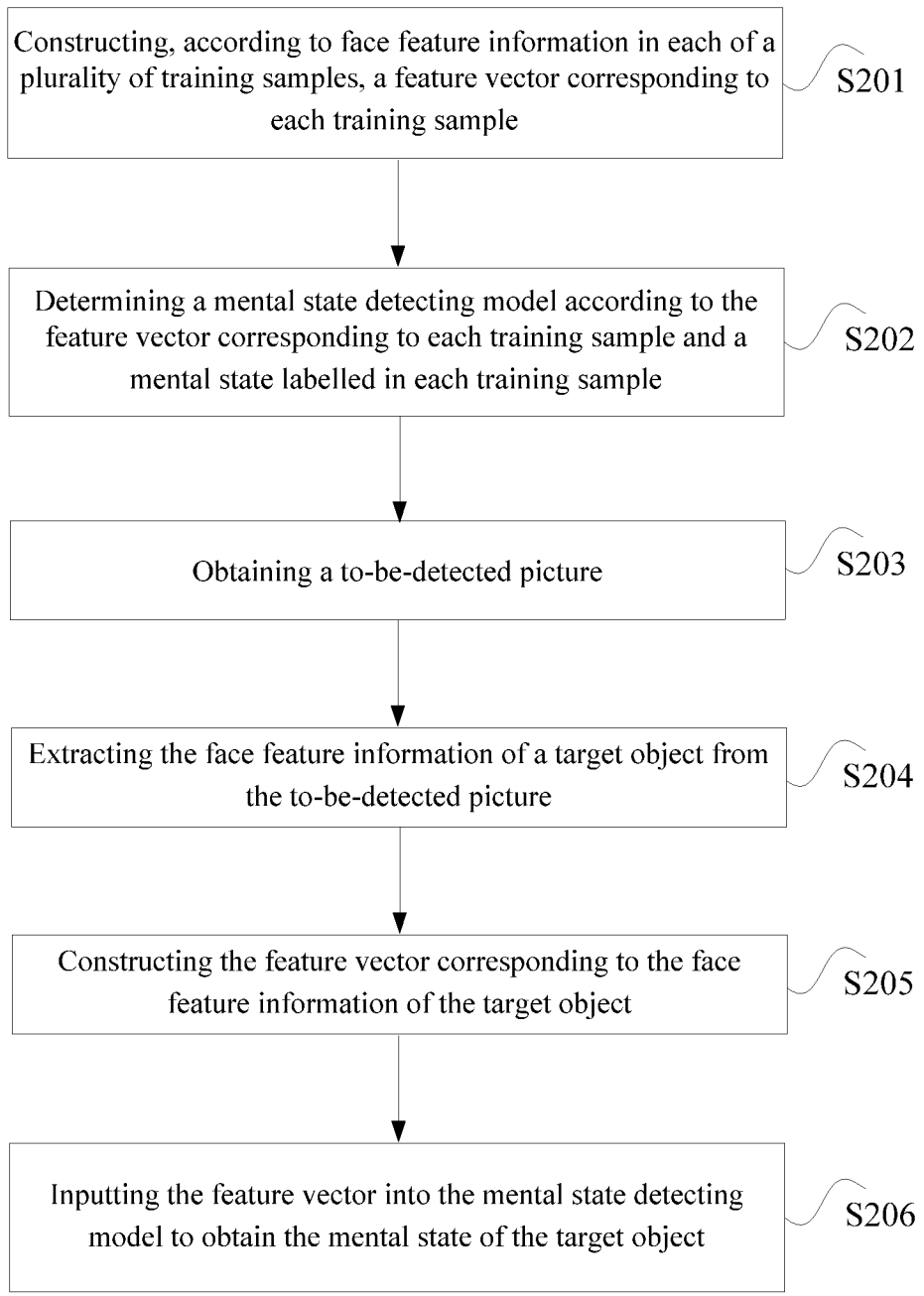
FIG. 2 is a schematic flowchart diagram of another method for determining a mental state of a human according to an embodiment of the present disclosure.

Based on the embodiment shown in FIG. 1, in order to more clearly describe the method for determining a mental state of a human shown in the embodiments of the present disclosure, for example, reference is made to FIG. 2 which is a schematic flowchart diagram of another method for determining a mental state of a human according to an embodiment of the present disclosure, and the method for determining a mental state of a human may further include:

S201: constructing, according to the face feature information in each of a plurality of training samples, a feature vector corresponding to each training sample.

In an embodiment, the face feature information of the target object includes at least one of the following: a degree of eye openness, whether red veins exist in an eye, a color of an eye socket, a size of a pouch under the eye, and a state of skin. Further, the state of the skin may include a skin gloss and the like.

In the embodiment of the present disclosure, the plurality of training samples may be determined first, and an amount of the training samples is not specifically limited. Of course, the more the selected training samples, the higher the accuracy of the final trained mental state detecting model. Here, each training sample includes face feature information, and after the face feature information in each training sample is obtained, it is possible to construct, according to the face feature information in each training sample, the feature vector corresponding to the training sample.

S202: determining the mental state detecting model according to the feature vector corresponding to each training sample and the mental state labelled in each training sample.

It should be noted that, for each training sample, the mental state corresponding to the face feature information in the training sample is labelled in the training sample. For example, if a certain training sample has a low degree of eye openness, red veins in the eye, a black eye socket, a large pouch under the eye, and dull skin, the mental state of the object is very bad, and correspondingly, the mental state of the training sample can be labelled as a bad mental state; on the contrary, a relatively high degree of eye openness, no red veins in the eye, no black eye socket, a small pouch under the eye, and good skin gloss, indicate that the mental state of the object is very good and correspondingly, the mental state of the training sample can be labelled as a good mental state.

After the feature vector corresponding to each training sample and the mental state labelled in each training sample are obtained respectively, it is possible to train the feature vector corresponding to each training sample and the mental state labelled in each training sample by using a deep learning method, so as to obtain the mental state detecting model. Of course, it is also possible to train the feature vector corresponding to each training sample and the mental state labelled in each training sample by using other methods so as to obtain the mental state detecting model. Here, training the feature vector corresponding to each training sample and the mental state labelled in each training sample by using the deep learning method so as to obtain the mental state detecting model is only taken as an example for illustration in the embodiments of the present disclosure, but this does not represent the embodiments of the present disclosure are limited only thereto.

It should be labelled that, for S201-S202, it is not always necessary to perform S201-S202 every time the mental state of the target object is determined, and the mental state detecting model may be established only at a time that the mental state of the target object is determined for a first time. Of course, in order to further improve the accuracy of the mental state detecting model, the mental state detecting model can be continuously trained and revised, thereby improving the accuracy of the mental state detecting model.

After the mental state detecting model is obtained, it is possible to determine the mental state of the target object through the mental state detecting model. Of course, before the mental state of the target object is determined, a to-be-detected picture of the target object needs to be obtained first, that is, S203 needs to be performed as follows:

S203: obtaining the to-be-detected picture.

Similarly, the to-be-the detected picture includes the face feature information of the target object.

For obtaining the to-be-detected picture, the to-be-detected picture may be obtained in advance by a terminal. Of course, the to-be-detected picture may also be obtained in a real-time manner by the terminal. How to obtain the to-be-detected picture is not further limited in the embodiments of the present disclosure.

S204: extracting the face feature information of the target object from the to-be-detected picture.

In an embodiment, for extracting the face feature information of the target object, it is possible to extract the face feature information of the target object from the to-be-detected picture through a feature extraction technology, and reference may be made to the related description of the feature extraction technology in the prior art, which will not be repeated in the embodiments of the present disclosure.

For example, when the target object is San Zhang, after a photo of San Zhang is obtained, the face feature information of San Zhang can be extracted from the photo, which may include: a low degree of eye openness, some red veins existing in an eye, a dark color of an eye socket, a large pouch under the eye, and a poor skin gloss of San Zhang.

It should be noted that an order of performing S201-S202 and S203-S204 is not specified in the embodiments of the present disclosure. It is possible to perform S201-S202 first and then S203-S204; it is also possible to perform S203-S204 first and then S201-S202. Of course, S201-S202 and S203-S204 may be simultaneously performed. Here, performing S201-S202 first and then S203-S204 is only taken as an example for illustration in the embodiments of the present disclosure, but this does not represent that the embodiments of the present disclosure are limited only thereto.

S205: constructing the feature vector corresponding to the face feature information of the target object.

After the face feature information of the target object is extracted from the to-be-detected picture through the above S204, according to the face feature information of the target object, the feature vector corresponding to the face feature information can be constructed and thereby be used as an input into the trained mental state detecting model to obtain the mental state of the target object.

For example, after the face feature information of San Zhang is extracted, it is possible to construct, according to the face feature information of San Zhang, such as a low degree of eye openness, some red veins existing in an eye, a dark color of an eye socket, a large pouch under the eye and a poor skin gloss, the feature vector corresponding to such face feature information, and the feature vector corresponding to the face feature information of San Zhang, such as the low degree of eye openness, some red veins existing in the eye, the dark color of the eye socket, the large pouch under the eye and the poor skin gloss, can be used as the input into the trained mental state detecting model to obtain the mental state of San Zhang.

S206: inputting the feature vector into the mental state detecting model to obtain the mental state of the target object.

Similarly, for outputting the mental state of the target object, it is possible to directly output a category of the mental state, such as a very poor mental state, a poor mental state, a general mental state, a good mental state, and a very good mental state. Of course, it is also possible to output a quantized value of the mental state, and the mental state is quantified as a score segment. For example, a score segment of 0-20 points corresponds to the very poor mental state, a score segment of 20-40 points corresponds to the poor mental state, a score segment of 40-60 points corresponds to the general mental state, a score segment of 60-80 points corresponds to the good mental state, and a score segment of 80-100 points corresponds to the very good mental state. Here, these two output modes are only taken as an example for illustration in the embodiments of the present disclosure, but this does not represent that the embodiments of the present disclosure are limited only thereto.

After the feature vector corresponding to the face feature information of the target object is obtained through the above S205, the feature vector corresponding to the face feature information, as an input into the trained mental state detecting model, can be input into the mental state detecting model and the mental state of the target object can be obtained thereby, which, in comparison with determining the mental state of the target object by a measuring device in the prior art, does not need to obtain physiological characteristics of the target object via a measuring device, and then to determine the mental state of the target object according to the physiological characteristic information, thereby not only improving the mental state obtaining efficiency, but also improving the accuracy of the obtained mental state.

For example, after the feature vector corresponding to the face feature information of San Zhang, such as a low degree of eye openness, some red veins existing in an eye, a dark color of an eye socket, a large pouch under the eye and a poor skin gloss, as an input into the trained mental state detecting model, is input into the mental state detecting model, a poor mental state of San Zhang may be obtained, which, in comparison with determining the mental state of San Zhang by a measuring device in the prior art, does not need to obtain physiological characteristics of San Zhang via a measuring device, and then to determine the mental state of San Zhang according to the physiological characteristic information, thereby not only improving the mental state obtaining efficiency, but also improving the accuracy of the obtained mental state.

Figure 3:
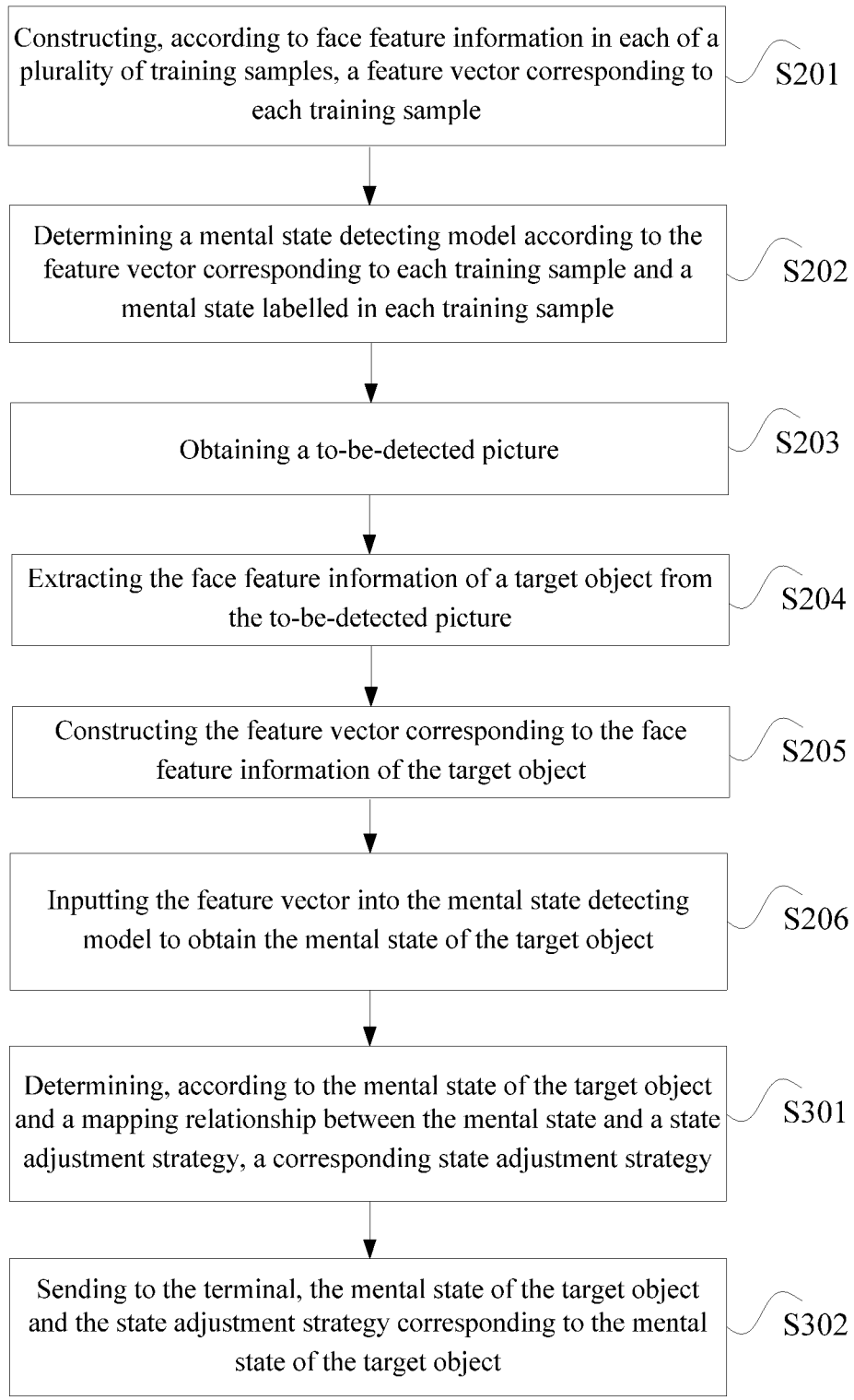
FIG. 3 is a schematic flowchart diagram of yet another method for determining a mental state of a human according to an embodiment of the present disclosure.

Based on the embodiments illustrated in FIG. 1 or FIG. 2, in an embodiment, after the face feature information of the target object is input into the mental state detecting model through S206 and the mental state of the target object is obtained, it is also possible to send the mental state of the target object to a terminal so that the target object can get its own mental state. In addition, a corresponding health suggestion (i.e., a state adjustment strategy) may be determined for the mental state of the target object, and the state adjustment strategy may be sent to the target object, so that the target object makes an adjustment according to the state adjustment strategy. For example, reference is made to FIG. 3 which is a schematic flowchart diagram of yet another method for determining a mental state of a human according to an embodiment of the present disclosure, and the method for determining a mental state of a human may further include:

S301: determining, according to the mental state of the target object and a mapping relationship between the mental state and the state adjustment strategy, a corresponding state adjustment strategy.

For example, the mapping relationship between the mental state and the state adjustment strategy may be pre-stored in a server, so that after the mental state of the target object is obtained, the state adjustment strategy corresponding to the mental state of the target object can be determined according to the pre-stored mapping relationship between the mental state and the state adjustment strategy.

For example, when it is determined through the above S201-S206 that the mental state of San Zhang is poor, the state adjustment strategy corresponding to the poor mental state of San Zhang may be determined according to the pre-stored mapping relationship between the mental state and the state adjustment strategy. For example, such state adjustment strategy may include increasing sleep time, improving diet, exercising more, and the like.

S302: sending to the terminal, the mental state of the target object and the state adjustment strategy corresponding to the mental state of the target object.

After the mental state of the target object and the state adjustment strategy corresponding to the mental state of the target object are determined respectively, the mental state of the target object and the corresponding state adjustment strategy thereto may be sent to the terminal, so that the terminal may display the mental state of the target object in a manner of using the augmented reality (AR) technology, so that the target object can view its mental state through the terminal in time, and perform a health adjustment according to the corresponding state adjustment strategy, thereby improving its mental state.

For example, after the poor mental state of San Zhang and the state adjustment strategy corresponding to the poor mental state of San Zhang are determined respectively, the mental state of San Zhang and the corresponding state adjustment strategy thereto can be sent to the terminal, so that San Zhang can view his mental state in time through the terminal, and make a health adjustment according to the corresponding state adjustment strategy to improve his mental state.

Figure 4:
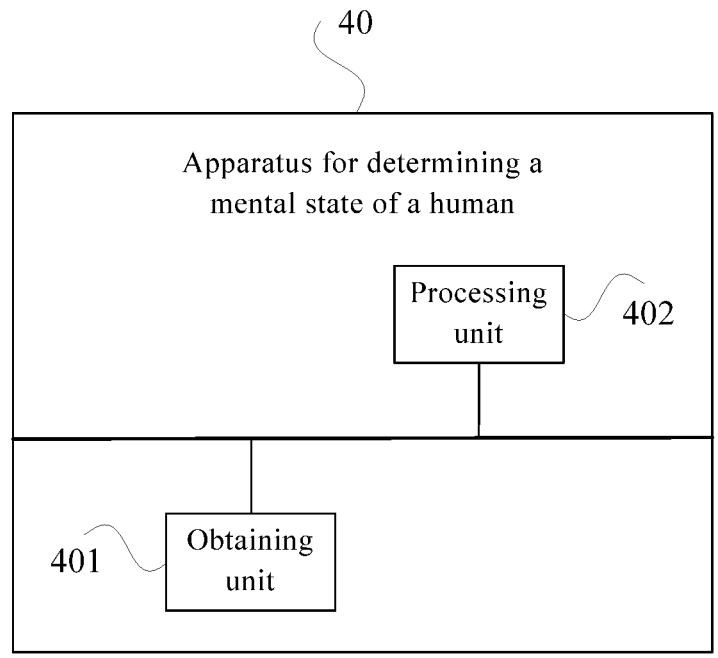
FIG. 4 is a schematic structural diagram of an apparatus for determining a mental state of a human according to an embodiment of the present disclosure.

FIG. 4 is a schematic structural diagram of an apparatus 40 for determining a mental state of a human according to an embodiment of the present disclosure. Reference is made to FIG. 4, and the apparatus 40 for determining a mental state of a human can be applied to an augmented reality, and can include:

an obtaining unit 401 configured to obtain a to-be-detected picture;

the obtaining unit 401 being further configured to extract face feature information of a target object from the to-be-detected picture; and a processing unit 402 configured to input the face feature information of the target object into a mental state detecting model to obtain the mental state of the target object.

In an embodiment, the face feature information of the target object includes at least one of the following:

a degree of eye openness, whether red veins exist in an eye, a color of an eye socket, a size of a pouch under the eye, and a state of skin.

In an embodiment, the processing unit 402 is specifically configured to: construct a feature vector corresponding to the face feature information of the target object; and input the feature vector into the mental state detecting model to obtain the mental state of the target object.

Figure 5:
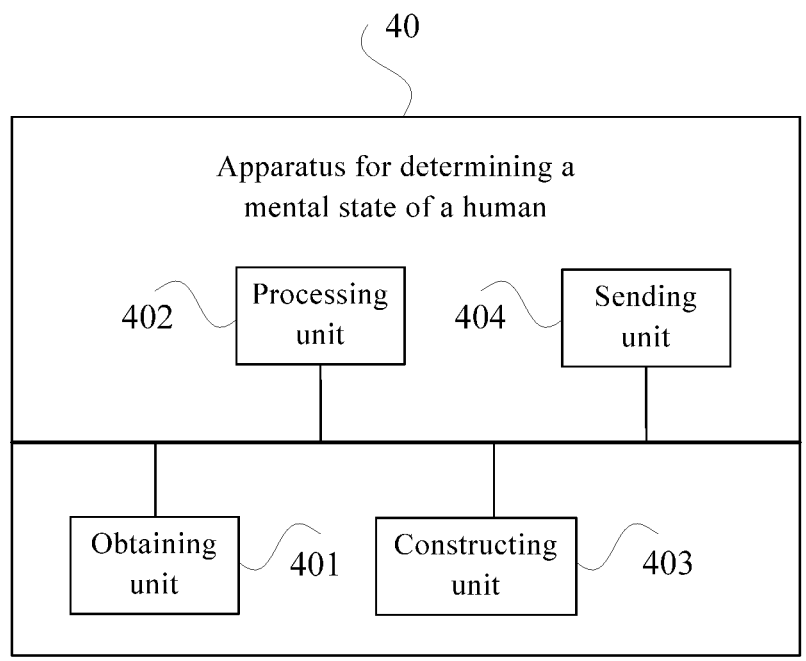
FIG. 5 is a schematic structural diagram of another apparatus for determining a mental state of a human according to an embodiment of the present disclosure.

In an embodiment, the apparatus 40 for determining a mental state of a human further includes a constructing unit 403. For example, reference is made to FIG. 5 which is a schematic structural diagram of another apparatus for determining a mental state of a human according to an embodiment of the present disclosure.

The mental state detecting model is trained by following: the constructing unit 403 is configured to construct, according to the face feature information in each of a plurality of training samples, a feature vector corresponding to each training sample.

The processing unit 402 is further configured to determine the mental state detecting model according to the feature vector corresponding to each training sample and the mental state labelled in each training sample.

In an embodiment, the processing unit 402 is specifically configured to train, by using a deep learning method, the feature vector corresponding to each training sample and the mental state labelled in each training sample to obtain the mental state detecting model.

In an embodiment, the apparatus 40 for determining a mental state of a human further includes a sending unit 404.

The processing unit 402 is further configured to determine, according to the mental state of the target object and a mapping relationship between a mental state and a state adjustment strategy, a corresponding state adjustment strategy.

The sending unit 404 is configured to send, to a terminal, the mental state of the target object and the state adjustment strategy corresponding to the mental state of the target object.

The apparatus 40 for determining a mental state of a human described in the embodiments of the present disclosure can perform the technical solutions of the method for determining a mental state of a human described in any of the above embodiments. The implementation principles and the beneficial effects are similar, which are not repeated here.

Figure 6:
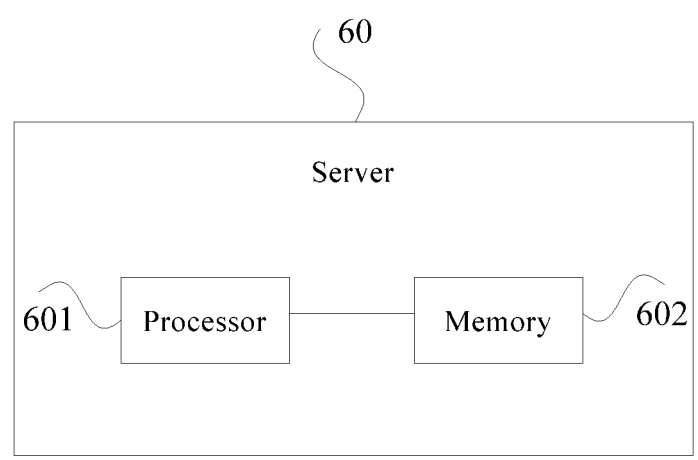
FIG. 6 is a schematic structural diagram of a server according to an embodiment of the present disclosure.

FIG. 6 is a schematic structural diagram of a server 60 according to an embodiment of the present disclosure. Reference is made to FIG. 6, and the server 60 may include a processor 601 and a memory 602.

The memory 602 is configured to store a program instruction.

The processor 601 is configured to read the program instruction in the memory 602 and execute the method for determining a mental state of a human illustrated by any of the embodiments described above, according to the program instruction in the memory 602.

The server 60 described in the embodiments of the present disclosure may perform the technical solutions of the method for determining a mental state of a human described in any of the above embodiments. The implementation principles and the beneficial effects are similar, which are not repeated here.

An embodiment of the present disclosure further provides a computer readable storage medium, where the computer readable storage medium stores a computer program, and the computer program, when executed by a processor, performs the method for determining a mental state of a human described in any of the above embodiments. The implementation principles and the beneficial effects are similar, which are not repeated here.

In the foregoing embodiment, the processor may be a general purpose processor, a digital signal processor (DSP), an application specific integrated circuit (ASIC), a field programmable gate array (FPGA), or other programmable logic device, a discrete gate or a transistor logic device, or a discrete hardware component, which may implement or execute the methods, steps, and logical block diagrams disclosed in the embodiments of the present disclosure. The general purpose processor may be a microprocessor or the processor may be any conventional processor or the like, which in combination with the steps of the method disclosed in the embodiments of the present disclosure may be directly embodied as implementing the steps by a hardware decoding processor, or by a combination of hardware and software modules in the decoding processor. The software module can be located in a random access memory (RAM), a flash memory, a read-only memory (ROM), a programmable read only memory or an electrically erasable programmable memory, a register, or any other form of storage medium known in the art. The storage medium is located in the memory, and the processor reads the instructions in the memory and is combined with the hardware to complete the steps of the above method.

In the embodiments provided by the present disclosure, it should be understood that the disclosed apparatus and method may be implemented in other manners. For example, the apparatus embodiments described above are merely illustrative. For example, the division of the unit is only a logical function division. In actual implementation, there may be another division manner, for example, multiple units or components may be combined or can be integrated into another system, or some features can be ignored or not executed. In addition, the mutual coupling or direct coupling or communication connection shown or discussed may be an indirect coupling or communication connection through some interface, apparatus or unit, and may be in an electrical, mechanical or other form.

The units described as separate components may or may not be physically separated, and the components displayed as units may or may not be physical units, that is, may be located in one place, or may be distributed to multiple network units. Some or all of the units may be selected according to actual needs to achieve the purpose of the solution of the embodiment. In addition, each functional unit in each embodiment of the present disclosure may be integrated into one processing unit, or each unit may exist physically separately, or two or more units may be integrated into one unit. The above integrated unit can be implemented in the form of hardware or in the form of hardware plus software functional units.

After considering the specification and practicing the disclosure disclosed herein, those skilled in the art will easily come up with other implementations of this disclosure. The present disclosure is intended to cover any variations, uses, or adaptations of this disclosure, which are in accordance with the general principles in this disclosure and include common knowledge or common technical means in the art that are not disclosed in this disclosure. The specification and embodiments are to be regarded as illustrative only. The true scope and spirits of this disclosure is defined by the following claims.

It is to be understood that this disclosure is not limited to the exact structure described above and illustrated in the accompanying drawings and may be modified and changed without departing from the scope of this disclosure. The scope of this disclosure is limited only by the accompanying claims.

What is claimed is:

1. A method for determining a mental state of a human, wherein the method is used for an augmented reality and comprises:
   obtaining a to-be-detected picture;
   extracting face feature information of a target object from the to-be-detected picture; and
   inputting the face feature information of the target object into a mental state detecting model to obtain a mental state of the target object;
   wherein after the inputting the face feature information of the target object into a mental state detecting model to obtain a mental state of the target object, the method further comprises:
   determining, according to the mental state of the target object and a mapping relationship between the mental state and a state adjustment strategy, a corresponding state adjustment strategy; and
   sending to a terminal, the mental state of the target object and the state adjustment strategy corresponding to the mental state of the target object.

2. The method according to claim 1, wherein:
   the face feature information of the target object comprises at least one of following:
   a degree of eye openness, whether red veins exist in an eye, a color of an eye socket, a size of a pouch under the eye, and a state of skin.

3. The method according to claim 1, wherein the inputting the face feature information of the target object into a mental state detecting model to obtain a mental state of the target object comprises:
   constructing a feature vector corresponding to the face feature information of the target object; and
   inputting the feature vector into the mental state detecting model to obtain the mental state of the target object.

4. The method according to claim 1, wherein the mental state detecting model is trained by following means:
   constructing, according to a face feature information in each of a plurality of training samples, a feature vector corresponding to each training sample; and
   determining the mental state detecting model according to the feature vector corresponding to each training sample and a mental state labelled in each training sample.

5. The method according to claim 4, wherein the determining the mental state detecting model according to the feature vector corresponding to each training sample and the mental state labelled in each training sample comprises:
   training, by using a deep learning method, the feature vector corresponding to each training sample and the mental state labelled in each training sample to obtain the mental state detecting model.

6. An apparatus for determining a mental state of a human, wherein the apparatus is used for an augmented reality, and comprises a processor, a transmitter and a memory storing instructions thereon, the processor when executing the instructions, being configured to:

obtain a to-be-detected picture;

extract face feature information of a target object from the to-be-detected picture; and input the face feature information of the target object into a mental state detecting model to obtain the mental state of the target object;

the processor is further configured to determine, according to the mental state of the target object and a mapping relationship between a mental state and a state adjustment strategy, a corresponding state adjustment strategy; and the transmitter is configured to send, to a terminal, the mental state of the target object and the state adjustment strategy corresponding to the mental state of the target object.

7. The apparatus according to claim 6, wherein:

the face feature information of the target object comprises at least one of following:

a degree of eye openness, whether red veins exist in an eye, a color of an eye socket, a size of a pouch under the eye, and a state of skin.

8. The apparatus according to claim 6, wherein the processor is further configured to:

construct a feature vector corresponding to the face feature information of the target object; and input the feature vector into the mental state detecting model to obtain the mental state of the target object.

9. The apparatus according to claim 6, wherein the processor is further configured to:

construct, according to a face feature information in each of a plurality of training samples, a feature vector corresponding to each training sample; and determine the mental state detecting model according to the feature vector corresponding to each training sample and a mental state labelled in each training sample.

10. The apparatus according to claim 9, wherein the processor is further configured to train, by using a deep learning method, the feature vector corresponding to each training sample and the mental state labelled in each training sample to obtain the mental state detecting model.

11. A computer readable storage medium, wherein:

the computer readable storage medium stores a computer program, and the computer program, when executed by a processor, implements the steps of:

obtaining a to-be-detected picture;

extracting face feature information of a target object from the to-be-detected picture;

inputting the face feature information of the target object into a mental state detecting model to obtain the mental state of the target object;

determining, according to the mental state of the target object and a mapping relationship between a mental state and a state adjustment strategy, a corresponding state adjustment strategy; and sending, to a terminal, the mental state of the target object and the state adjustment strategy corresponding to the mental state of the target object.

12. The computer readable storage medium according to claim 11, wherein:

the face feature information of the target object comprises at least one of following:

a degree of eye openness, whether red veins exist in an eye, a color of an eye socket, a size of a pouch under the eye, and a state of skin.

13. The computer readable storage medium according to claim 11, wherein the storage medium further comprises computer execution instruction which, when executed by the processor, implements the steps of:

constructing a feature vector corresponding to the face feature information of the target object; and inputting the feature vector into the mental state detecting model to obtain the mental state of the target object.

14. The computer readable storage medium according to claim 11, wherein the storage medium further comprises computer execution instruction which, when executed by the processor, implements the steps of:

constructing, according to the face feature information in each of a plurality of training samples, a feature vector corresponding to each training sample; and determining the mental state detecting model according to the feature vector corresponding to each training sample and the mental state labelled in each training sample.

15. The computer readable storage medium according to claim 14, wherein the storage medium further comprises computer execution instruction which, when executed by the processor, implements the steps of:

training, by using a deep learning method, the feature vector corresponding to each training sample and the mental state labelled in each training sample to obtain the mental state detecting model.

* * * * *